(12) United States Patent
Kasper et al.

(10) Patent No.: US 8,586,029 B2
(45) Date of Patent: Nov. 19, 2013

(54) PREVENTION OR TREATMENT OF IMMUNE-RELEVANT DISEASE BY MODIFICATION OF MICROFLORAL POPULATIONS

(75) Inventors: Lloyd H. Kasper, Norwich, VT (US); Javier Ochoa-Repáraz, Enfield, NH (US)

(73) Assignee: Trustees of Dartmouth College, Hanover, NH (US)

( * ) Notice: Subject to any disclaimer, the term of this patent is extended or adjusted under 35 U.S.C. 154(b) by 297 days.

(21) Appl. No.: 12/993,909

(22) PCT Filed: Jun. 3, 2009

(86) PCT No.: PCT/US2009/046074
§ 371 (c)(1),
(2), (4) Date: Nov. 22, 2010

(87) PCT Pub. No.: WO2009/149149
PCT Pub. Date: Dec. 10, 2009

(65) Prior Publication Data
US 2011/0086011 A1   Apr. 14, 2011

Related U.S. Application Data

(60) Provisional application No. 61/058,769, filed on Jun. 4, 2008, provisional application No. 61/061,820, filed on Jun. 16, 2008.

(51) Int. Cl.
*A01N 63/00* (2006.01)

(52) U.S. Cl.
USPC ..................................... 424/93.71

(58) Field of Classification Search
None
See application file for complete search history.

(56) References Cited

U.S. PATENT DOCUMENTS

| 7,807,154 | B2 * | 10/2010 | Strasburger et al. | 424/130.1 |
| 2002/0022019 | A1 | 2/2002 | Laulund | 424/93.45 |
| 2005/0101012 | A1 * | 5/2005 | Schuler et al. | 435/372 |
| 2005/0271643 | A1 | 12/2005 | Sorokulova et al. | 424/93.462 |
| 2006/0014717 | A1 | 1/2006 | Angstrom et al. | 514/54 |
| 2007/0238747 | A1 | 10/2007 | van Duzer et al. | 514/279 |
| 2008/0131445 | A1 * | 6/2008 | Bluestone et al. | 424/184.1 |

OTHER PUBLICATIONS

Wexler, 2007, Clin.Microbio. Rev. vol. 20: 593-621.*
Burgers, 2005, Best Pract Res Clin Gyn vol. 19: 277-291.*
Dadley-Moore, 2005, Immune Regulation, pp. 1-2.*
Progress in Autoimmune Disease res.2005, pp. 1-126.*
Mazmanian et al., 2005, Cell. vol. 122: 107-118.*
Mor et al., 2005, J. Immunol. vol. 175: 3439-45.*
Zhang et al., 2004, Int. Immunol. vol. 16: 249-256.*
Jia et al. "Gut Microbia: a Potential New Territory for Drug Targeting" Nature Reviews Drug Discovery 2008 vol. 7(2): 123-129.
Krinos et al. "Extensive Surface Diversity of a Commensal Microorganism by Multiple DNA Inversions" Nature 2001 vol. 414: 555-561.
Macpherson et al. "IgA Responses in the Intestinal Mucosa Against Pathogenic and Non-Pathogenic Microorganisms" Microbes and Infection 2001 vol. 3 (12) : 1021-1035.
Mora et al. "Selective Imprinting of Gut-Homing T Cells by Peyer's Patch Dendritic Cells" Nature 2003 vol. 424: 88-93.
Mora et al. "Generation of Gut-Homing IgA-Secreting B Cells by Intestinal Dendritic Cells" Science 2006 vol. 314: 1157-1160.
Niess et al. "Commensal Gut Flora Drives the Expansion of Proinflammatory CD4 T Cells in the Colonic Lamina Propria under Normal and Inflammatory Conditions" The Journal of Immunology 2008 vol. 180: 559-568.
Oda, K. and Kitano, H. "A Comprehensive Map of the Toll-Like Receptor Signaling Network" Molecular Systems Biology 2006.15: 1-20.
Verdù et al. "Oral Administration of Antigens from the Intestinal Flora Anaerobic Bacteria Reduces the Severity of Experimental Acute Colitis in BALB/c Mice" Clinical & Experimental Immunology 2000 vol. 120: 46-50.
Wagner, M.A. "Use of Reporter Cells to Study Endogenous Retinoid Sources in Embryonic Tissues" Methods in Enzymology 1997 vol. 282 Vitamins and Coenzymes Part L: 98-107.
Woessner et al. "Long-Term Antibiotic Treatment with Roxithromycin in Patients with Multiple Sclerosis" Infection 2006 vol. 34(6): 342-344.
Zabad et al. "The Clinical Response to Minocycline in Multiple Sclerosis is Accompanied by Beneficial Immune Changes: a Pilot Study" Multiple Sclerosis 2007 vol. 13: 517-526.

* cited by examiner

*Primary Examiner* — Amy Juedes
(74) *Attorney, Agent, or Firm* — Licata & Tyrrell, P.C.

(57) ABSTRACT

The present invention is a method for preventing or treating an immune-relevant disease by modulating commensal microbiota populations via antibiotics, exogenous microbiota and/or probiotics.

3 Claims, 2 Drawing Sheets

PREVENTION OR TREATMENT OF IMMUNE-RELEVANT DISEASE BY MODIFICATION OF MICROFLORAL POPULATIONS

INTRODUCTION

This application is the national phase under 35 U.S.C. §371 of PCT International Application No. PCT/US2009/46074, filed Jun. 3, 2009, which claims benefit of U.S. Provisional Patent Application Ser. Nos. 61/058,769 filed Jun. 4, 2008 and 61/061,820 filed Jun. 4, 2008, the contents of which are incorporated herein by reference in their entireties.

BACKGROUND OF THE INVENTION

Oral tolerance has been associated with the control of experimental autoimmune diseases including experimental autoimmune encephalomyelitis, the animal model of human multiple sclerosis (MS). In tolerance, low antigen dose appears to suppress, whereas higher doses induce clonal anergy. Tolerance depends on polarization to a Th2 (IL-4, IL-10) and/or Th3 (TGF-β) phenotype. Regulatory $CD4^+CD25^+$ $T_{reg}$ cells, as well as IL-4, IL-10, anti-IL-12p40, TGF-β, and anti-CD40 ligand enhance tolerance (Weber, et al. (2007) Nat. Med. 13:935). Oral antigens such as MBP or glatiramer acetate, an FDA approved therapy for relapsing-remitting multiple sclerosis have been shown to suppresses EAE (Weber, et al. (2007) supra).

Studies have demonstrated that tolerance induction through oral immunization with foreign antigens can control the development of autoimmune diseases. Oral immunization with a single dose of an attenuated strain of Salmonella Typhimurium expressing the CFA/I fimbriae of Enterotoxigenic E. coli confers prophylactic and therapeutic protection against EAE in SJL mice (Jun, et al. (2005) J. Immunol. 175:6733). Salmonella-CFA/I elicits $FoxP3^+CD4^+CD25^+$ $T_{reg}$ cells that produce TGF-β (Ochoa-Reparaz (2007) J. Immuno. 178:1791), and although a switch to Th-2 type immune responses played a role in diminishing EAE, the role of $T_{reg}$ cells was clearly predominant. Adoptive transfer of Salmonella-CFA/I-induced $T_{reg}$ cells, but not naïve $T_{reg}$ cells, protected against EAE, suggesting that the immunization with Salmonella, an irrelevant non-self bacterial antigen, induced and expanded $T_{reg}$ cells in mice that were protective against EAE (Ochoa-Reparaz (2007) supra).

Similarly, it has been shown that dextran sodium sulphate-induced colitis can be suppressed by oral administration of antigens from normal intestinal flora anaerobes (Verdù, et al. (2000) Clin. Exp. Immunol. 120:46-50).

Although mammals are born sterile, microorganisms soon colonize their mucosal surfaces after birth. The colonization of the mucosal surface of the gut evolves into a highly diverse endogenous microflora population composed of over $10^{13}$ resident bacteria, creating a relationship that confers benefits to both microorganisms and host (Hooper & Gordon (2001) Science 292:1115). However, this environment can be shared by multiple pathogens that utilize the mucosa as invasion and infection sites. It is the role of the immune system to concurrently control the responses to commensal and pathogenic organisms. It is possible that changes in the microbial composition of the intestinal compartments modify the phenotype, proliferation and functional capacity of regulatory T cells. In this regard, it has been suggested that the significant involvement of the gut microbiota in human health and disease indicates that manipulation of commensal microbial composition through combinations of antibiotics, probiotics and prebiotics could be a novel therapeutic approach (Jia, et al. (2008) Nat. Rev. Drug Discov. 7(2):123-9).

The role of regulatory T cells in the induction of tolerance has been analyzed (Weiner (2001) Microbes Infect. 3:947; Zhang & Zhao (2007) J. Cell Physiol. 211:590; Pascual, et al. (2007) Endocr. Metab. Immune Disord. Drug Targets 7:203; Sakaguchi, et al. (2007) Eur. J. Immunol. 37 Suppl 1:S11). Retinoic acid expressed by $CD103^+$ gut-derived dendritic cells in the presence of TGF-β appears essential to the conversion of naïve $CD4^+CD25$-effector T cells into a regulatory $FoxP3^+T_{reg}$ cells subpopulation (Weiner (2001) supra; Zhang & Zhao (2007) supra; Pascual, et al. (2007) supra). $T_{reg}$ cells expressing the surface trafficking molecule α4β7 migrate specifically to the gut mucosa linking the expression of retinoic acid to the conversion and migration of $T_{reg}$ cells. It has been demonstrated that the metabolism of vitamin A into retinoic acid appears to depend on the presence of commensal bacteria (Schambach, et al. (2007) Eur. J. Immunol. 37:2396). Absence of bacteria in germ-free mice (axenic) that are born and raised in sterile isolators demonstrates that the presence of commensal bacteria is essential for normal immune development. Alterations in the immune profile in these mice exhibit a default Th2 bias and a significant reduction in proinflammatory IL-17-producing $CD4^+$ T cells compared to mice with an intact communal gut bacterial profile (Niess, et al. (2008) J. Immunol. 180:559).

Bacteroides fragilis, a gram-negative anaerobe, is the prototypic member of the microflora in the normal mammalian gut (Niess, et al. (2008) supra). Genomic analysis has shown that B. fragilis is able to produce eight different capsular polysaccharides (PSA-PSH) with on-off phase variable phenotypes that may be involved in the broad adaptability of this bacteria to different mammalian hosts (Krinos, et al. (2001) Nature 414:555). Studies have demonstrated that at least one of these polysaccharides, the zwitterrionic polymer PSA is able to induce the activation and proliferation of $CD4^+$ T cells. Moreover, PSA controls the Th1/Th2 physiologic balance in germ-free animals colonized with Bacteroides fragilis and immunized with purified PSA (Mora, et al. (2003) Nature 424:88; Mora, et al. (2006) Science 314:1157). Gut colonization in germ-free mice demonstrated that PSA is able to interact with TLR2 signaling in dendritic cells (DCs) and stimulate T cell activation (Mora, et al. (2003) supra). Immunization with purified PSA expanded T cell populations in both germ-free and intact mice, increased MHC class II expression among $CD11c^+$ DCs and the expression of CD80 and CD86 (Mora, et al. (2006) supra). Interestingly, germ-free animals have a default Th2 bias with increased production of IL-4 and low levels of IFN-γ as opposed to intact animals (Massacesi, et al. (1987) J. Neurol. Sci. 80:55; Macpherson, et al. (2001) Microbes Infect. 3:1021; Iwata, et al. (2004) Immunity 21:527). When germ-free mice were infected with B. fragilis, the IL-4 levels were significantly reduced while IFN-γ production was restored (Mora, et al. (2006) supra). Infection of germ-free mice with B. fragilis deficient in PSA did not provoke this cytokine profile switching (Mora, et al. (2006) supra).

It has been observed that retinoic acid induces the homing of leukocytes to the gut. The peripheral homing preferences of T cells to migrate to a specific tissue are imprinted by DCs from that tissue during antigen presentation (Mora, et al. (2003) supra). DCs from the gut Mesenteric lymph nodes (MLN) and Peyer's patches (PP) induces the gut-homing markers α4β7 and CCR9 on T cells, while DCs from peripheral lymph nodes (PLN) induced, preferentially, the skin homing receptors P- and E-selectin ligands. Based on this observation and the observation that Vitamin A deficiency impairs gut immunity, the function of retinoic acid on the expression of homing receptors on T cells has been evaluated (Mora, et al. (2003) supra). In these experiments, CD4+ T cells were stimulated with αCD3 and αCD28 in the presence or absence of retinoic acid. The addition of retinoic acid enhanced the expression of α4β7 and the mRNA levels of CCR9, together with the suppression of E-selectin ligand expression. This effect was not impaired when T cells were cultured under Th1 or Th2 skewing conditions. In addition, CD4+ T cells cultured in the presence of retinoic acid showed increased migration to the CCR9 ligand, TECK, when tested in trans-well experiments. Performing competitive homing experiments in vivo, it was observed that retinoic acid-treated CD4+ T cells migrated preferentially to the gut, in comparison with untreated CD4+ T cells. Furthermore, the potential population of cells synthesizing retinoic acid in vivo was determined by the expression of the enzyme RALDH. It was observed that MLN- and PP-DCs, but not PLN-DCs, express RALDH. In addition, MLN- and PP-DC but not splenic DCs were able to convert retinol to retinoic acid. This work was the first to demonstrate that the migration of T cells to the gut is due to the retinoic acid secreted by gut-resident DCs, and also to confirm the importance of Vitamin A in gut immunology. It must be noted that the stromal cells in the MLN and PP also stained for RALDH, and so while it is clear that the DCs did produce retinoic acid, it is conceivable that stromal cells may contribute to this effect.

Studies have explored the function of gut DC loaded with commensal bacteria and the effect on IgA production (Macpherson, et al. (2001) supra). CD11c+ cells were purified from the PP and MLN of mice challenged with a known commensal (*E. clocae*). DC from mice gavaged with live bacteria demonstrated a rise in IgA+B cells and an increase in the production of IgA that was absent from mice treated with heat-killed bacteria. The increased response to live bacteria was not dependent on the presence of either B cells or T cells. DCs appear to be key in class switch recombination reaction to express IgA. Further studies in specific pathogen-free mice that were colonized with a simple flora demonstrated that there was a five-fold increase of IgA producing cells in the lamina propria following inoculation with high numbers of commensal bacteria of several different gram positive or negative strains. This enhanced IgA response to commensal inoculation was dependent on the uptake of the live bacteria that had penetrated the epithelial layer by CD11c+ DC and subsequent stimulation of B and T cell responses.

It has been suggested that commensal bacteria and the host immune system constitute an integrated defense system (Kitano & Oda (2006) *Mol. Systems Biol.* 2:2006.0022), wherein this symbiotic association has evolved to optimize its robustness against pathogen attacks and nutrient perturbations by harboring a broad range of microorganisms. Owing to the inherent propensity of a host immune system toward hyperactivity, it has been suggested that maintenance of bacterial flora homeostasis might be particularly important in the development of preventive strategies against immune disorders such as autoimmune diseases. While antibiotics such as minocycline (Zabad, et al. (2007) *Mult. Scler.* 13(4):517-26) and roxithromycin (Woessner, et al. (2006) *Infection* 34(6): 342-4) have been evaluated, e.g., to determine systemic immunological changes and identify a causative connection between bacterial infections with *C. pneumonia* and multiple sclerosis, the effect of these antibiotics on commensal bacteria was not demonstrated.

SUMMARY OF THE INVENTION

The present invention is a method for preventing or treating an immune-relevant disease by modulating commensal microbiota populations in a subject in need of treatment. In accordance with one embodiment, an effective amount of one or more antibiotics are administered to the subject to modulate commensal microbiota populations. In other embodiments, the antibiotic is administered in combination with exogenous microflora or one or more probiotics.

The present invention also features a method for transferring protection to an immune-relevant disease from one subject to another. The method involves isolating regulatory T cells from a first subject colonized with a *Bacteroides* and administering said regulatory T cells to a second subject having an immune-relevant disease so that protection to the immune-relevant disease is transferred from the first subject to the second subject.

DETAILED DESCRIPTION OF THE INVENTION

Figure 1:
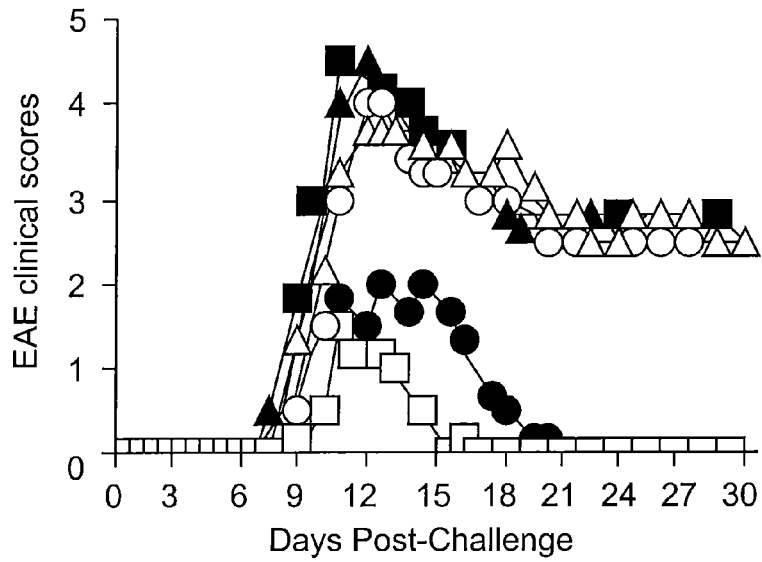
FIG. 1 shows that antibiotic treatment against gut microflora, as well as subsequent reconstitution with wild-type *B. fragilis* reduces EAE clinical scores.

Oral tolerance has been associated with the control of experimental autoimmune diseases including experimental autoimmune encephalomyelitis (EAE), the most widely used animal model of human multiple sclerosis (MS). Oral antigens have been shown to suppress EAE, providing evidence that oral tolerance can be elicited in this demyelinating inflammatory condition. It has now been shown that commensal bacteria can control peripheral immunity and the balance of tolerance in adaptive and innate pathways. These findings are relevant to further the understanding of disease pathogenesis, since in autoimmune diseases the homeostatic regulation of the balance between an effective immune response against foreign antigens and auto-reactive responses appears to be disrupted.

Accordingly, the present invention relates to the use of gut commensal bacteria as mediators of immune homeostasis in the gut and the periphery. In particular, gut commensal bacteria disclosed herein have the effect of modifying $T_{reg}$ cell percentages in GALT and other peripheral lymphoid tissues. Further, the invention relates to modification of gut commensal bacteria in the prevention and treatment of immune-relevant diseases such as EAE and human multiple sclerosis. Moreover, the invention embraces the use of intestinal bacteria, such as *Bacteroides fragilis*, expressing capsular polysaccharides including, but not limited to PSA, PSB, PSC, PSD, PSE, PSF, PSG, or PSH, in regulating immune homeostasis. Not wishing to be bound by any theory, it is believed that there are several mechanisms by which this bacterial antigen can affect disease activity including the induction, amplification and proliferation of $T_{reg}$ cells; the enhancement of $T_{reg}$ cell migration and trafficking to the CNS; and protection against disease progression. These $T_{reg}$ responses can provide insight into the role of gut commensal bacteria during relapses and remission in multiple sclerosis. Thus, the invention relates to the modification of the composition of commensal bacteria for providing an immune regulatory effect against the development and progression of immune-relevant disease such as EAE and human multiple sclerosis.

In the context of the present invention, modification is intended to mean an increase or decrease in the gut microbiota populations or ratios. In particular embodiments, the absolute or relative numbers of desirable gut microorganisms is increased and/or the absolute or relative numbers of undesirable gut microorganisms is decreased. It is contemplated that there are a variety of ways in which the gut microbiota populations or ratios can be modulated. In a particular embodiment, modification is achieved by the oral administration of one or more antibiotics. The antibiotic(s) employed can specifically target a particular species or genus of gut microorganism or multiple species or genera of microorganisms to modulate the relative or absolute numbers of one or more gut microorganisms. In accordance with this embodiment of the invention, the modification of gut microflora is all that is required to cause a beneficial immune system response and prevent or treat an immune-relevant disease.

Antibiotics of use in accordance with the present invention include those disclosed herein (i.e., ampicillin, vancomycin, neomycin sulfate and metronidazole) as well as any other suitable antibiotic including but not limited to, Amoxicillin, Alatrofloxacin, Tetracycline, Moxifloxacin, Azithromycin, Bacampicillin, Oxacillin, Benzylpenicillin, Clarithromycin, Carbenicillin, Cefadroxil, Cephalexin, Cefditoren, Cefepime, Cefmetazole, Cefoperazone, Cefprozil, Cephalexin, Clarithromycin, Clindamycin, Daptomycin, Dicloxacillin, Erythromycin, Gemifloxacin, Sulfamethoxazole, Kanamycin, Levofloxacin, Lincomycin, Lomefloxacin, Vancomycin, Meropenem, Nafcillin, Nalidixic Acid, Tobramycin, Piperacillin, Polymyxin, Trimethoprim, Rifampin, Streptomycin, Trovafloxacin, and combinations thereof. In so far as extended administration (e.g., 2, 3, 4 or more weeks) has been shown to confer full protection against EAE in mice, antibiotic(s) can be administered in single or multiple doses for acute or chronic periods of time. The amount of antibiotic employed desirably reduces bacterial load, the gut microbiota composition, or ratios of particular species of bacteria. While the antibiotic can be administered via any suitable route, particular embodiments embrace oral administration.

In accordance with another embodiment of the invention, the administration of antibiotics is combined with the administration of exogenous microflora (e.g., one or more beneficial bacteria and/or yeast). Desirably, the exogenous microflora is compatible with the endogenous microflora and once administered produces the beneficial effect of modulating the immune system. Desirably, the exogenous microflora is one which is a natural component of the microflora or microbiota of the mammalian gut, i.e., a microorganism or commensal that normally lives in the digestive tract. Most bacteria of the intestinal microbiota come from the genera *Bacteroides, Clostridium, Fusobacterium* (Beaugerie & Petit (2004) *Best Practice & Research Clinical Gastroenterology* 18:337-352; Guarner & Malagelada (2003) *Lancet* 361:512-519; Vedantam & Hecht (2003) *Curr. Opin. Microbiol.* 6:457-461), *Eubacterium, Ruminococcus, Peptococcus, Peptostreptococcus,* and *Bifidobacterium* (*B. adolescentis. B. bifidum* and *B. longum*) (Guarner & Malagelada (2003) supra; Beaugerie & Petit (2004) supra). Other genera such as *Escherichia* and *Lactobacillus* are also present to a lesser extent (Beaugerie & Petit (2004) supra). In so far as species from the genus *Bacteroides* constitute about 30% of all bacteria in the gut, particular embodiments of the present invention embrace a bacterium from the genus *Bacteroides*. Species of *Bacteroides* embraced by the present invention include *B. ovatus, B. thetaiotaomicron, B. fragilis,* and *B. intestinalis*, wherein *B. fragilis* is desirably employed. In particular embodiments, the exogenous microflora is a capsular polysaccharide-producing bacterium. As used herein, a "capsular polysaccharide-producing bacterium" or "exogenous microflora that produces a capsular polysaccharide" is a bacterium which produces or secretes a capsular polysaccharide.

As indicated, the bacterium of the present invention expresses one or more capsular polysaccharides including, but not limited to, PSA, PSB, PSC, PSD, PSE, PSF, PSG, or PSH. The bacterium can naturally express the capsular polysaccharide or be genetically engineered to express the capsular polysaccharide. In this regard, any bacterial member of the intestinal microbiota can be genetically engineered to express a capsular polysaccharide which originates in another member of the intestinal microbiota. For example, the biosynthetic locus of polysaccharide B from *B. fragilis* 9343 (Comstock, et al. (1999) *Infect. Immun.* 67:3525-3532) can be genetically engineered into a strain of *Lactobacillus*. Similarly, the locus required for the synthesis of polysaccharide A from *B. fragilis* 9343 has been identified (Coyne, et al. (2001) *Infect. Immun.* 69(7):4342-50) and can be recombinantly expressed in any suitable member of the intestinal microbiota. In particular embodiments of the present invention, the capsular polysaccharide is a zwitterionic capsular polysaccharide that utilizes MHCII presentation to activate T cells. An exemplary zwitterionic capsular polysaccharide is polysaccharide-A (PSA) produced by *B. fragilis*.

Heterologous expression of biosynthetic gene clusters in bacteria is routinely practiced in the art and any suitable method can be employed. See, e.g., Aso, et al. (2004) *J. Biosci. Bioeng.* 98:429-436. In particular, heterologous expression of the polysaccharide biosynthetic genes in *Lactococcus lactis* is conventional. See, e.g., Gilbert, et al. (2000) *Infect. Immun.* 68:3251-3260 and Lamothe, et al. (2002) *Arch. Microbiol.* 178: 218-228.

In accordance with yet another embodiment of the invention, one or more probiotics are employed either alone or in combination with one or more antibiotics to modulate commensal bacteria populations. As used herein, a probiotic is defined as a live microorganism which when administered in adequate amounts confers a health benefit on the host. Probiotic cultures are intended to assist the body's naturally occurring gut flora, an ecology of microbes, to re-establish themselves. Members of the lactic acid bacterial group are generally considered probiotic organisms, wherein the best-known probiotic is *Lactobacillus acidophilus*. Yeasts such as *Saccharomyces boulardii* are also embraced as probiotics of the present invention.

It is further contemplated that the modification of endogenous microfloral populations can be achieved by modification of pH or other environmental factors, physical methods including localized heating, radiation, mechanical removal, or other methods of reducing bacterial counts, or administration of any of a variety of small molecule, peptidic, inorganic, or cellular moieties which modify absolute and/or relative populations of endogenous microflora. Moieties of any of these types which preferentially enable growth of endogenous *Bacteroides* populations are particularly embraced by this invention.

Agents disclosed herein for modulating commensal microbiota populations are desirably administered directly to the gastrointestinal tract as a suppository, or delivered orally as a capsule, gel cap, pill, or tablet. When administered orally, the agents can have an enteric coating so that the agent reaches the intestine of the subject intact, i.e., not degraded or killed. In particular, enteric coating can be used to facilitate the delivery of viable bacteria. Alternatively, the agents of the invention can be administered in the form of a nutraceutical, dietary supplement or powder, health bar, yogurt, or the like. Formulation and administration of such agents is routinely practiced in the art and any suitable formulation can be employed.

The agents of the invention can be administered as a single daily dose, or as multiple doses depending on the agent, the health of the subject, and the immune-relevant disease being treated. Moreover, the agents can be administered simultaneously or consecutively (e.g., within a day, week or month of one another).

As indicated, the present invention embraces the prevention or treatment of an immune-relevant disease by modification of commensal microbiota populations in a subject. An immune-relevant disease is a disease in which the immune system is a significant factor in the development and/or progression of the disease, or in which the immune system can be advantageously employed to cause disease regression. Examples of immune-relevant diseases include, but are not limited to autoimmune diseases such as multiple sclerosis, Crohn's disease, rheumatoid arthritis and the like; as well as cancer and HIV. In particular embodiments the immune-relevant diseases is multiple sclerosis. Immunotherapies which additively or synergistically include the use of commensal microflora modification are also embraced by this invention, as are commensal-regulated immunotherapies for Alzheimer's disease.

According to the present invention, a subject in need of treatment, i.e., a subject having or at risk of developing an immune-relevant disease such as multiple sclerosis, is administered an effective amount of an agent (e.g., an antibiotic, exogenous microbiota, or probiotic), which modulates commensal microbiota populations. A subject having an immune-relevant disease generally exhibits one or more of the typical signs or symptoms of the immune-relevant disease, whereas a subject at risk of developing an immune-relevant disease has one or more risk factors (e.g., genetic predisposition or exposure to chemical agents) which predispose the subject to the immune relevant disease. By way of illustration, a subject with multiple sclerosis can exhibit one or more of the following signs or symptoms: muscle weakness, abnormal muscle spasms, or difficulty in moving; ataxia; dysarthria or dysphagia, nystagmus, optic neuritis, diplopia, acute or chronic pain syndromes, or bladder and bowel difficulties); whereas a subject at risk of developing multiple sclerosis includes subjects with, e.g., a deficiency of vitamin D during childhood (Munger, et al. (2006) *JAMA* 296:2832-8). As is conventional in the art, prevention means that a disease does not develop as a result of the administration of the therapeutic agent, whereas treatment means a decrease in progression, reversal or amelioration of one or more signs or symptoms of the disease being treated. Such outcomes have been demonstrated herein and can be routinely determined by the skilled clinician.

As demonstrated herein, regulatory T cells isolated from mice colonized with the wild-type *B. fragilis* are protective when adoptively transferred into mice four days after EAE induction. Accordingly, the present invention also features a method for transferring protection to an immune-relevant disease from one subject to another. The method involves isolating regulatory T cells from a first subject colonized with a *Bacteroides* and administering said regulatory T cells to a second subject having an immune-relevant disease so that protection to the immune-relevant disease is transferred from the first subject to the second subject. For the purposes of the present invention, a subject "colonized with a *Bacteroides*" is intended to mean that the subject has a detectable population of *Bacteriodes* in the gastrointestinal tract. The transfer of regulatory T cells can be carried out as disclosure herein or using any other suitable method.

In addition to the agents disclosed herein, it is contemplated that therapeutic agents can be developed that alter the commensal bacteria and give rise to disease modification. Such therapies would alter the gut flora thereby providing an alternative to conventional therapies that are clearly focused on shifting the host immune response by either blockade or ablation leading to a more regulatory phenotype.

The invention is described in greater detail by the following non-limiting examples.

EXAMPLE 1

Materials and Methods

Mice.

Female, six-week old SJL/J mice were obtained from The Jackson Laboratories (Bar Harbor, Me.). All mice were maintained under pathogen-free conditions in individual ventilated cages under HEPA-filtered barrier conditions and were fed sterile food and water ad libitum.

Oral Immunizations with Purified PSA.

Mice were treated orally with 50 µg of purified PSA every other 3 days after EAE induction.

Antibiotic Treatments in Drinking Water and Bacterial Reconstitution.

SJL mice were treated with the following antibiotics dissolved in drinking water: Ampicillin (1 g/ml), vancomycin (0.5 g/ml), neomycin sulfate (1 g/ml) and metronidazole (1 g/ml) (Rakoff-Nahoum, et al. (2004) *Cell* 118:229-41). When required, dissolved antibiotics were administered by i.p. injections at daily single doses of 1 g/ml. Serial dilutions of intestinal and fecal samples were cultured in general bacteriological agar plates (CDC blood agar; BD, Sparks, Md.) for 48 hours at 37° C. Plates were cultured in aerobic and anaerobic conditions. Total bacteria/gram of sample was calculated based on the colony forming units (CFU) counted in each serial dilution.

Wild-type *Bacteroides fragilis* (WT *B. fragilis*) (NCTC 9343) and PSA-deficient *B. fragilis* (ΔPSA *B. fragilis*) are known in the art (Mazmanian, et al. (2005) *Cell* 122:107-118). Mice were infected with $10^{10}$ WT or ΔPSA *B. fragilis* resuspended in 200 μl of sterile PBS by oral gavage.

Microarray Analysis of Commensal Bacteria Populations.

Fresh fecal samples of mice were collected on days 0 and 7 of treatment with antibiotics, and day 7 after reconstitution with WT or ΔPSA *B. fragilis*. Samples were snap frozen and stored at −80° C. Total DNA from mice fecal samples was obtained using a modified extraction protocol of the QIAMP DNA Stool mini kit (QIAGEN Inc., Valencia, Calif.). Extraction yields and DNA concentrations were measured with a NANODROP ND-1000 spectophotometer (NanoDrop Technologies, Wilmington, Del.). The microarray analysis of small subunit ribosomal RNA (SSU rRNA) gene sequences of commensal bacteria populations was carried out according to standard conditions (Fiocco, et al. (2009) *J. Bacteriol.* 191(5):1688-94; Troost, et al. (2008) *BMC Genomics* 9:374).

$PLP_{139-151}$ Challenge. The encephalitogenic PLP peptide ($PLP_{139-151}$; HSLGKWLGHPDKF; SEQ ID NO:1) was synthesized by Peptides International (Louisville, Ky.), and HPLC-purified to >90%. For each experiment, female SJL mice (4/group) were challenged s.c. with 200 μg $PLP_{139-151}$ in 200 μl of Complete Freunds Adjuvant (Sigma). On days 0 and 2 post-challenge, mice received i.p. 200 ng of *Bordetella pertussis* toxin (PT; List Biological Laboratories, Campbell, Calif.) (Ochoa-Reparaz, et al. (2007) *J. Immunol.* 178:1791-9). Control groups were treated with PBS. Mice were monitored and scored daily for disease progression (Ochoa-Reparaz, et al. (2007) supra): 0, normal; 1, a limp tail; 2, hind limb weakness; 3, hind limb paralysis; 4, quadriplegia; 5, death.

Histological Evaluation of Spinal Cords.

For histological evaluation, spinal cords were harvested 12 days after challenge and fixed with neutral buffered formalin (VWR International, West Chester, Pa.), embedded into paraffin, and sectioned at 3 μm. Transverse sections of spinal cords were stained with H&E for pathological changes and inflammatory cell infiltration. Adjacent sections were stained with luxol fast blue (LFB) and examined for loss of myelin. Pathological manifestations were scored separately for cell infiltrates and demyelination. Each H&E section was scored from 0 to 4: 0, normal; 1, cell infiltrate into the meninges; 2, one to four small focal perivascular infiltrates; 3, five or more small focal perivascular infiltrates and/or one or more large infiltrates invading the parenchyma; 4, extensive cell infiltrates involving 20% or more of the white matter (Ochoa-Reparaz, et al. (2007) supra). In each LFB stained section, myelin was also scored from 0 to 4: 0, normal; 1, one small focal area of demyelination; 2, two or three small focal areas of demyelination; 3, one to two large areas of demyelination; 4, extensive demyelination involving 20% or more of white matter.

Cytokine Detection by LUMINEX

Spleens and cervical lymph nodes (CLNs) were aseptically harvested from naïve mice and from mice treated with antibiotics for 7 days. Cell suspensions were resuspended in complete medium (CM): RPMI 1640 medium supplemented with 1 mM sodium pyruvate, 1 mM nonessential amino acids (Gibco), penicillin/streptomycin (10 U/ml) (Gibco), and 10% fetal bovine serum (Atlanta Biologicals, Lawrenceville, Ga.). Lymphocytes were cultured in 24-well tissue plates at $2 \times 10^6$ cells/ml in CM alone or in the presence of anti-CD3 mAb-coated wells (10 μg/ml; BD Pharmingen), plus the soluble anti-CD28 mAb (5.0 μg/ml; BD Pharmingen) for 3 days in CM (final volume of 300 μl in 24-wells plate) (Ochoa-Reparaz, et al. (2007) supra). LUMINEX was employed to quantify triplicate sets of samples to measure IFN-γ, TNF-α, MIP-1α, MIP-1β, MCP-1, IL-6, IL-17, IL-4, IL10, and IL-13 cytokines.

PCR Detection of Cytokine mRNA.

A total of 1.0 μg of QIAGEN RNEASY-purified (QIAGEN) mRNA was reverse-transcribed using MULTI-SCRIBE RT (Amersham Biosciences AB, Uppsala, Sweden). A total of 200 ng of cDNA was amplified using the ×2 SYBR green mix (Applied Biosystems) on a BIO-RAD iCycler. Relative expression was normalized to β-actin and was expressed using the CT method, where relative expression=2^(exp−actin)*1000. PCR detection of IL-13 mRNA was carried out with primers 5'-GGT CCT GTA GAT GGC ATT GCA-3' (SEQ ID NO:2) and 5'-GG AGC TGA GCA ACA TCA CAC A-3' (SEQ ID NO:3).

FACS Analysis.

Lymphocytes from the Peyer's Patches (PPs), MLNs, spleens and CLNs were isolated from naïve mice, mice treated with antibiotics, and treated with antibiotics and subsequently colonized with wild-type *B. fragilis* or ΔPSA *B. fragilis* 12 days after challenge with $PLP_{139-151}$, and single cell preparations were prepared according to standard methods (Ochoa-Reparaz, et al. (2007) supra). Cells were stained for FACS analysis using conventional methods. T cell subsets were analyzed using fluorochrome-conjugated mAbs (BD Pharmingen) for CD3, CD4, CD8, CD45Rb and CD25 as indicated. Intracellular staining for FoxP3 and IFN-γ, IL-17, IL-13, IL10, IL-4 cytokines were performed using fluorochrome labeled-anti-Foxp3 mAb (clone FJK-16s; eBioscience, San Diego, Calif.) and PE labeled-anti-IFN-γ, IL-17, IL10, IL-4 (BD Pharmingen) and anti-IL-13 (eBiosciences). For macrophages and dendritic cell subpopulations, CD11b, CD11c, CD103, B220, CD8, Gr-1 and F4/80 mAb were used ((BD Pharmingen). For NK cells, DX5, B220 and CD11b were used. For B cells, CD19 and B220 (BD Pharmingen) were used. Bound fluorescence was analyzed with a FACS Canto (BD Biosciences, Mountain View, Calif.).

Retinoic Acid Detection in Tissues. Retinoic acid was detected in PPs and MLNs according to standard protocols (Wagner (1997) *Methods Enzymol.* 282:98-107). Briefly, a monolayer of retinoid reporter cell line was co-cultured with whole PPs overnight at 37° C. with 5% $CO_2$. After incubation, tissues were removed and cells were treated for 1 minute at 37° C. with FITC staining for gene reporter, and analyzed by FACS (Wagner (1997) *Methods Enzymol.* 282:98-107). The RA-inducible reporter cell line used was a lacZ reporter line derived from F9 teratocarcinoma cells transfected with an *E. coli* β-galactosidase reporter gene. This gene product is encoded under the control of a known retinoid response. Reporter enzymatic activity indicates the presence of retinoids released from sample tissues.

Cell Purifications.

CD11c+ cells were obtained with magnetic beads (Stem-Cell Technologies, Vancouver, Canada). The enriched $CD11c^+$ cells were cell-sorted (FACSVANTAGE with Turbo-Sort, BD Biosciences) following staining with FITC-anti-CD103 into $CD11c^{high}CD103^+$ cells. $CD4^+$ T cells and $CD8^+$ T cells were obtained with magnetic beads (Dynal Biotech ASA, Oslo, Norway). The enriched $CD4^+$ T cells were cell-sorted for FITC-anti-CD4 and APC-anti-CD25 mAbs (BD PharMingen) by FACS.

In Vitro Suppressive Assays and Adoptive Transfer Experiments.

Naïve CD25−CD4+ T cells ($1.5 \times 10^5$) were co-cultured in triplicate with $CD11c^{high}CD103^+$ in the presence or absence of retinoic acid (4 nM) and TGF-β (5 ng/ml). Anti-CD3 mAb (10 mg/ml; BD Pharmingen) and IL-2 (20 units/well) were added. Cells were incubated at 37° C. in 5% of $CO_2$ for 72 hours. Conversion of naïve CD25−CD4+ T cells into FoxP3+ $T_{reg}$ cells was compared by FACS. To assess $T_{reg}$ cell suppressor activity, $1.5 \times 10^5$ responder CD25−CD4+ T cells were labeled with CFSE and subsequently co-cultured in triplicate with CD25+CD4+ T cells at 1:1, 1:0.1, 1:0.01 and 1:0.001 CD25−:CD25+ T cell ratios. Feeder cell (T cell-depleted mitomycin C-treated) splenocytes prepared from naïve mice (Pascual, et al. (1999) Infect. Immun. 67:6249-56) were added at $1.5 \times 10^5$ cells per well. Cells were incubated at 37° C. in 5% of $CO_2$ for 72 hours. CD4+ T cell proliferation was compared by FACS. For adoptive transfer experiments, $4 \times 10^5$ CD25+CD4+ T cells or CD25−CD4+ T cells were i.v. injected into naïve recipients. One day after the adoptive transfer of T cells, mice were challenged with $PLP_{139-151}$ to induce EAE.

In Vivo Inactivation of CD25+CD4+ T Cells.

Mice were orally treated with antibiotics seven days prior to EAE challenge with $PLP_{139-151}$ and PT. To inactivate CD25+CD4+ T cells, the same mice were given 0.3 mg of anti-CD25 mAb (ATCC #TIB-222, clone PC 61.5.3) on days 4 and 2 before EAE challenge (Ochoa-Reparaz, et al. (2007) supra). As a control group, treated and naïve mice received 0.3 mg of purified rat IgG antibody on the same days prior to EAE challenge. CD25 depletion was confirmed by FACS analysis of peripheral blood samples obtained 2 days after the administration of the second dose of anti-CD25 or rat IgG antibodies. A separate control group was immunized with PBS seven days prior to EAE challenge.

Statistical Analysis.

The student t test was applied to show differences of combined experiments in clinical scores, body, spleen and cecum weights, LUMINEX detection of cytokines as well as in the flow cytometry of $T_{reg}$ cell and DC experiments. ANOVA followed by post-hoc Tukey test was applied to show differences in EAE clinical scores. P-values <0.05 and <0.01 are indicated.

EXAMPLE 2

Oral Treatment with Antibiotics Reduces Commensal Microflora and Alters Immune Responses in the GALT and the Periphery C57BL/6 and SJL mice were treated with antibiotics in order to reduce the gut bacterial population (Wagner (1997) Methods Enzymol. 282:98). Ampicillin (1 g/ml), vancomycin (0.5 g/ml), neomycin sulfate (1 g/ml) and metronidazole (1 g/ml) were dissolved in drinking water and supplied to mice for seven days. Oral treatment with antibiotics reduced bacterial PFU by day 4-post treatment and significantly reduced the commensal populations from the fecal and intestinal samples of mice. Aerobic and anaerobic conditions were examined and in both cases, a significant reduction of bacterial counts was found one week after treatment. No bacterial CFU were detected in fecal samples of mice treated orally with antibiotics as opposed to the culture of fecal intestinal contents, suggesting that fresh pellets might be insufficient in order to compare total bacterial loads. Only oral but not i.p. treatment, with antibiotics reduced gut commensal microflora and altered significantly the morphology of the mice. However, antimicrobial treatment did not completely deplete bacterial presence showing that certain bacterial populations remain viable despite antibiotic treatment. When animals were subsequently provided with normal drinking water, intestinal re-colonization was observed one week later. The treatment with antibiotics does not render the gut sterile but rather substantially reduces the bacterial load and perhaps alters the composition of the normal gut microflora.

Oral antibacterial treatment also provoked morphological alterations in mice; splenic sizes were significantly reduced in treated mice (P<0.01) and significant increases in the size and weights of cecums (P<0.01) were observed when compared to naïve mice. Histological sections of the cecums showed no pathological signs. Increases of cecum sizes are weights have been described (Koopman, et al. (1986) Lab. Anim. 20:286-290). Bacterial re-colonization observed one week after the end of the antibiotics treatment was associated with partial restoration of body, spleen and cecum weights and sizes.

Mice were sacrificed on day 7 of antibiotic treatment and Peyer's Patches (PPs), mesenteric lymph nodes (MLNs), spleens and head and neck lymph nodes (HNLN) were aseptically removed and lymphocyte suspensions were prepared according to conventional methods. A control group of mice included treatment with the same antibiotics intraperitoneally (i.p.). $T_{reg}$ cells subsets were analyzed using fluorochrome-conjugated monoclonal antibodies specific for surface CD4 and CD25 antigens (R&D Systems, Minneapolis, Minn.). Intracellular staining for Foxp3 was accomplished using FITC-anti-Foxp3 monoclonal antibody (eBioscience, San Diego, Calif.). Bound fluorescence was analyzed with a FAC-SCANTO (BD Biosciences, Franklin Lakes, N.J.).

A major change in the GALT was observed, wherein a significant reduction (P<0.01) of $T_{reg}$ cells from the PP was evident but not the MLN of antibiotic-treated mice. Conversely, an increase in the $T_{reg}$ cell population was observed in the spleen (P<0.001) and cervical lymph nodes (P<0.001) following antibiotic treatment. Spleen and cervical nodes harvested from mice treated with antibiotics demonstrated a significant reduction in the percentage of CD25 expression in total CD4+ T cells analyzed. This reduction was not observed in spleens and HNLN, where microflora-depleted animals presented a significantly enhanced population in $T_{reg}$ cells when compared to normal mice. However, FoxP3 expression in CD4+CD25+ T cells was significantly diminished in microflora-depleted animals, even in spleens and HNLN.

Retinoic acid was also detected in Peyer's Patches according to established methods. Briefly, a monolayer of retinoid reporter cell line was co-cultured with whole Peyers Patches overnight at 37° C. with 5% $CO_2$. After incubation, tissues were removed and cells were treated for 1 minute at 37° C. with FITC staining for gene reporter, and analyzed by FACS (Wagner (1997) supra). The results of this analysis indicated that the amount of retinoic acid detected in PPs of C57, treated with antibiotics against gut microflora, was reduced when compared to the levels observed in PPs of normal mice. These results indicate that a reduction of retinoic acid in microflora-depleted mice can influence the FoxP3 expression in $T_{reg}$ cells.

Splenic and HNLN lymphocytes were harvested from naïve and mice treated orally with antibiotics and cultured for 72 hours in the presence of anti-CD3 and anti-CD28 antibodies and supernatants were used to quantify the production of cytokines by LUMINEX. Results showed that immune responses of antibiotic-treated mice were modified, and splenic and HNLN lymphocytes produced different patterns of cytokines when compared to control naïve mice. Alteration of commensal populations produced a significant reduction of splenic IFN-γ, MIP-1α, MIP-1β, MCP-1, and IL-6, whereas IL-13 was significantly enhanced when compared to naïve levels.

To further analyze this reduction in cytokines, Peyer's Patches (PP), Mesenteric LN (MLN), Splenic and Cervical LN (CLN) lymphocytes were harvested from naïve mice (Table 1) and mice treated orally with antibiotics and co-stimulated with αCD3/αCD28 antibodies (Table 2). Results show that the reduction of gut commensal microflora significantly diminished the production of MIP-1α, MIP-1β and IL-6 in PP. Mesenteric lymph nodes of animals treated with antibiotics produced lesser amounts of IFN-γ, MIP-1α, MIP-1β and IL-6, and significantly increased levels of IL-13. Splenic and CLN cells derived from these mice produced reduced IFN-γ, MIP-1α, MIP-1β, MCP-1, IL-17 and IL-6 levels, whereas IL-13, and IL-10 in CLN, were significantly enhanced when compared to untreated control mice. To study the cytokine pattern of mice treated with antibiotics and subsequently colonized with B. fragilis or ΔPSA B. fragilis, splenic lymphocytes were harvested from naïve and mice treated orally with antibiotics and stimulated ex vivo with αCD3/αCD28 antibodies. When treated mice were colonized with wild-type or ΔPSA B. fragilis, significant enhancements of IFN-γ and IL-10 production was observed. However, IL-10 production following reconstitution with ΔPSA B. fragilis was significantly lower than that observed following reconstitution with wild-type B. fragilis. ΔPSA B. fragilis colonization enhanced very significantly IL-6, as well as IL-17, whereas this increase was not seen following colonization with the wild-type bacteria expressing PSA. Interestingly, wild-type B. fragilis induced significant increases in the expression of the transcription factor GATA-3 and SMAD-3 when compared to ΔPSA.

TABLE 1

| Cytokine | Cytokine Concentration (pg/ml) | | | |
| --- | --- | --- | --- | --- |
| | PP | MLN | SPL | CLN |
| IFN-γ | 311 ± 27 | 798 ± 150 | 3500 ± 110 | 2761 ± 110 |
| TNF-α | 11.2 ± 2 | 10.8 ± 2.0 | 67.3 ± 12 | 140 ± 64 |
| MIP-1α | 910 ± 270 | 1102 ± 112 | 4050 ± 270 | 3142 ± 310 |
| MIB-1β | 3510 ± 758 | 4220 ± 250 | 20853 ± 988 | 17045 ± 461 |
| MCP-1 | 381 ± 21 | 433 ± 151 | 1545 ± 230 | 2090 ± 152 |
| IL-6 | 619 ± 84 | 761 ± 78 | 1598 ± 120 | 1040 ± 430 |
| IL-17 | 131 ± 55 | 831 ± 150 | 820 ± 430 | 1642 ± 321 |
| IL-4 | 101 ± 20 | 110 ± 81 | 273 ± 103 | 216 ± 31 |
| IL-10 | 81 ± 11 | 320 ± 51 | 144 ± 41 | 252 ± 47 |
| IL-13 | 210 ± 27 | 185 ± 6.3 | 405 ± 99 | 322 ± 101 |

TABLE 2

| Cyto-kine | Cytokine Concentration (pg/ml) | | | |
| --- | --- | --- | --- | --- |
| | PP | MLN | SPL | CLN |
| IFN-γ | 304 ± 78 | 380 ± 30* | 900 ± 430* | 2522 ± 310 |
| TNF-α | 14 ± 8.1 | 14.2 ± 3.0 | 43 ± 8.2 | 121 ± 13 |
| MIP-1α | 708 ± 70* | 818 ± 77± | 3100 ± 43* | 741 ± 28* |
| MIB-1β | 3040 ± 652* | 4177 ± 321 | 15120 ± 50* | 14230 ± 63* |
| MCP-1 | 334 ± 82 | 120 ± 30.2* | 110 ± 31* | 410 ± 411* |
| IL-6 | 434 ± 22* | 331 ± 21* | 99 ± 22* | 622 ± 73* |
| IL-17 | 110 ± 31 | 201 ± 20* | 265 ± 12* | 1121 ± 103* |
| IL-4 | 122 ± 77 | 131 ± 14 | 255 ± 41 | 210 ± 23 |
| IL-10 | 94 ± 8.2 | 313 ± 40 | 123 ± 24 | 391 ± 12* |
| IL-13 | 194 ± 42 | 731 ± 75* | 1130 ± 67* | 886 ± 118* |

*P < 0.05 for cytokine levels of naïve vs. antibiotic treated mice in each tissue analyzed.

EXAMPLE 3

Oral Treatment with Antibiotics Alters Immune Cell Populations

Flow cytometry was used to compare the populations of T cells, B cells, dendritic cells (DC), macrophages, natural killer (NK) cells and NKT cells. A significant reduction in CD4$^+$ T cells and enhanced CD8$^+$ T cells response was observed in mice treated orally with antibiotics when compared to naïve and i.p. treated mice. Phenotypic analysis of the various immune compartments within the PP of animals treated orally with antibiotics showed a significant reduction in T, B and CD11c$^+$CD11b$^+$ DC percentages. Conversely, there was a significant increase in CD11c$^+$CD11b$^+$ DCs when compared to either naïve or mice treated i.p. with the same antibiotic cocktail. Percentages of CD11b$^+$F4/80$^+$ monocytes, NK and NKT cells of treated mice failed to show any significant difference when compared to untreated control mice. The MLN of mice treated with oral antibiotics showed a significant reduction in total T cells, but no change in B, CD11b$^+$F4/80$^+$ monocytes, NK, NKT or CD11c$^+$CD11b$^+$ or CD11b$^-$ DC populations. The percentage of splenic T cells was significantly higher in orally treated than naïve and i.p. treated mice. No alterations were observed in CD11c$^+$CD11b$^+$, CD11c$^+$CD11b$^-$ and CD11c$^+$Gr-1$^+$ DCs, CD11b$^+$F4/80$^+$ monocytes. A significant reduction in NK and NKT cell percentages in the spleen was observed in mice after oral treatment with antibiotics. Analysis of CLN showed that percentages of T cells were reduced significantly in mice treated orally with antibiotics, with no modifications in the rest of cellular populations compared.

Oral treatment with antibiotics altered significantly CD4$^+$ T cell subpopulations. FACS analysis revealed that the frequency of CD4$^+$CD25$^+$ T cells was reduced in PP of mice orally treated with antibiotics, but significantly increased (P<0.01) in MLN, spleens and CLN when compared to naïve and i.p. treated mice. Lymph nodes of treated mice showed reciprocal reduction and enhancement of activated CD45Rb$^{low}$CD4$^+$ T cells in MLN and CLN of CD25$^+$ T cell populations when compared to naïve and mice treated i.p. with antibiotics. FACS analysis showed that oral treatment with antibiotics provoked a significant reduction (P<0.01) in the frequency of FoxP3$^+$CD25$^+$/total CD4$^+$ T cells in spleens but otherwise unchanged from control values. When total numbers of FoxP3$^+$T$_{reg}$ cell were compared, significant reductions (P<0.01) were measured in PP and spleens of mice subjected to oral treatment with antibiotics. However, gut flora alterations enhanced FoxP3$^+$ T$_{reg}$ cell numbers significantly (P<0.01) in MLN and CLN when compared to naïve and mice treated i.p. These results indicate that a combination of Th2-type immune responses and the induction of regulatory T cell subpopulations may provide an important framework that can offer protection against EAE when bacterial communities of the gut are challenged with antibiotics.

Alterations in FoxP3$^+$ T$_{reg}$ cells were further analyzed. It was determined whether the commensal Bacteroides and the presence of PSA in B. fragilis would affect the regulation of the immune system of these animals. SJL mice were colonized by gavage with B. fragilis or with ΔPSA B. fragilis on day 0 post antibiotic treatment and T$_{reg}$ cell populations were analyzed 3, 7 and 10 days gut post-colonization in PPs, MLNs, spleens or CLN. Mono-reconstitution with Bacteroides influenced the population of T$_{reg}$ cells in the gut-associated lymph nodes, spleen and CLN. FoxP3 expression levels in these T$_{reg}$ cells analyzed remained above 70%. Total numbers of FoxP3$^+$T$_{reg}$ cells were significantly enhanced in CLN of mice reconstituted with wild-type B. fragilis when compared to ΔPSA B. fragilis and control mice treated with antibiotics. Significant enhancement of FoxP3$^+$T$_{reg}$ cells in total CD4$^+$ T cells were seen in spleens and CLN of wild-type vs ΔPSA B. fragilis reconstituted mice. These results indicate that the presence of bacteria in the gut is associated with global immune homeostasis, not only within the GALT compartments but also in other peripheral immune sites, such as spleen and CLN.

EXAMPLE 4

Microflora-Mediated Protection Against EAE

In order to ascertain whether the alterations of the immune responses to modifications of gut commensal composition would alter the peripheral immune responses and global homeostasis, EAE was induced with $PLP_{139-151}$ in naïve and SJL mice previously treated with antibiotics (FIG. 1). Control mice were treated with PBS and i.p. with the same antibiotics. There have been different reports implicating a direct neurological effect by injections of minocycline, a $2^{nd}$ generation type of tetracycline. Minocycline provides partial protection against EAE when combined with glatiramer acetate or IFN-β (Ruggieri, et al. (2008) *J. Neuroimmunol.* 197:140-146; Giuliani, et al. (2005) *J. Neuroimmunol.* 165:83-91) provoking a down-regulation in the antigen presentation capability of blood monocyte-derived DCs antigen presentation in mice and activation capability in MS patients (Ruggieri, et al. (2008) supra). FIG. 1 and Table 3 show that oral treatment with antibiotics previous to challenge with PLP reduced significantly the severity of EAE when compared to PBS control and i.p. treated animals.

TABLE 3

| Treatment[a] | Onset[b] | Mortality (%) | Cumulative Score[e] |
|---|---|---|---|
| PBS-rat IgG | 10.1 ± 0.5 | 37.5 | 56.2 ± 0.2 |
| PBS-aCD25 | 9.0 ± 0.7* | 75* | 95.2 ± 1.1* |
| Oral Treated-rat IgG | 11.7 ± 0.5 | 0 | 6 ± 0.1 |
| Oral Treated-aCD25 | 9.5 ± 0.4* | 25*,T | 47.7 ± 0.5*,T |
| i.p. Treated-rat IgG | 10.2 ± 0.7 | 50 | 70.1 ± 1.1 |
| i.p. Treated-aCD25 | 9.2 ± 0.7* | 75* | 97.5 ± 1.2* |

[a]SJL Mice were treated orally or i.p. with antibiotics and subsequently with 300 mg of rat IgG or anti-CD25 mAb on days 3 and 5. On day 7, mice were challenged s.c. with 200 mg $PLP_{139-151}$ in complete Freund's adjuvant and 200 ng PT i.p. (days 0 and 2 post-EAE induction);
[b]Mean day ± SEM of clinical disease onset;
[e]Cumulative clinical scores were calculated as the sum of all clinical scores from disease onset after day 25 post-challenge, divided by the number of mice in each group.
*p < 0.001 for PBS vs oral t and oral vs i.p. treatment, and oral vs i.p. treatment.
*P < 0.05 for rat IgG vs aCD25 treated among groups (PBS, oral or i.p. treated with antibiotics).
TP < 0.01 for oral treated-aCD25 vs PBS-aCD25 and i.p. treated-aCD25.

Whereas all PBS- and i.p.-treated mice developed clinical scores (12/12) with maximum scores 5, incidence in animals treated with antibiotics was lower (8/12) and showed maximum clinical scores 3. Significant differences were observed in the onset of the disease and the cumulative scores of PBS vs. i.p. vs. orally treated mice. Demyelination and nucleated cell infiltration levels were reduced in orally treated mice. No significant differences were observed between PBS- and IP-treated mice (Table 4). Moreover, no significant differences in bacterial counts, body, or splenic weights were observed in mice treated i.p. with antibiotics when compared to naïve mice, indicating that the protection observed was due to the modification of bacterial populations in the gut.

TABLE 4

| Treatment[a] | Onset[b] | Cumulative Score[c] | Demylination[d] | Infiltration[e] |
|---|---|---|---|---|
| PBS | 8.6 ± 0.2 | 57.6 ± 0.2 | 2.0 ± 0.3 | 3.5 ± 0.2 |
| Oral | 10.7 ± 0.5*,* | 7.6 ± 1.1*,* | 0.7 ± 0.2*,* | 0.8 ± 0.4*,* |
| i.p. | 8.2 ± 0.2 | 48.4 ± 1.7 | 2.8 ± 0.5 | 3.2 ± 0.7 |

[a]SJL were challenged s.c. with 200 mg $PLP_{139-151}$ in complete Freund's adjuvant and 200 ng PT i.p. on days 0 and 2. Mice were treated orally or i.p. with antibiotics or PBS for 7 days prior EAE induction;
[b]Mean day ± SEM of clinical disease onset;
[c]Cumulative clinical scores were calculated as the sum of all clinical scores from disease onset after day 25 post-challenge, divided by the number of mice in each group.
*p < 0.001 for PBS vs oral t and oral vs i.p. treatment;
[d]Mean score ± SEM of demyelination: of spinal cords was scored from 0 to 4 in each mouse separately, and the mean score ± SEM was calculated.
*p < 0.001 for PBS vs oral t and oral vs i.p. treatment;
[e]Mean score ± SEM of inflammation: the infiltration of nucleated cells into spinal cords was scored from 0 to 4 in each mouse separately, and the mean score and SEM were calculated.
*p < 0.001 for PBS vs oral t and oral vs i.p. treatment.

When mice were treated with the antibiotics during the entire length of the experiment, mice were fully protected with no evidence of disease development as determined by clinical score. These data indicate that intestinal colonization with certain bacterial population can evoke clinical disease consistent with EAE.

PCR analysis showed enhanced levels of IL-β expression in the brains of animals protected against EAE by oral treatment with antibiotics when compared to PBS treated mice and animals treated i.p. with antibiotics. No significant differences in IL-13 production were observed in brains of mice treated i.p. and control PBS-treated mice.

EXAMPLE 5

Wild-Type *B. Fragilis*-Converted FoxP3$^+$T$_{reg}$ Cells Confer Prophylactic and Therapeutic Protection Against EAE Flow cytometry analysis of the lymph nodes show that reconstitution of the gut with *B. fragilis* drives the enhancement of T$_{reg}$ cell populations. Thus, it was determined whether reconstitution with wild-type or ΔPSA *B. fragilis* could determine the conversion rates of CD4$^+$CD25$^-$ T$_{effector}$ cells into FoxP3$^+$T$_{reg}$ cells in the MLN. CD4$^+$CD25$^-$ T cells isolated from MLN of naïve mice treated with antibiotics, and mice treated with antibiotics and subsequently reconstituted with wild-type or ΔPSA *B. fragilis* were cultured in vitro for 4 days in the presence of IL-2 and increasing concentrations of TGF-β and retinoic acid. Highest T$_{reg}$ cell conversion levels of naïve CD25$^-$T cells were obtained at retinoic acid concentrations of 2 and 4 nM (not significant differences) and 0.5 and 5 ng/ml of TGF-β (not significant differences). When no additional retinoic acid was included in the cultured media, CD25$^-$T cells sorted from MLN of mice reconstituted with wild-type *B. fragilis* had significant enhanced levels of conversion into T$_{reg}$ cells when compared to the rest of the experimental groups. Significant increases in the conversion rates of wild-type *B. fragilis* CD25-T cells were still observed at retinoic acid concentrations of 2 nM (0.5 and 5 ng/ml of TGF-β). Conversion rates were significantly enhanced in all groups when TGF-β concentrations were approaching the optimal concentration (Niess, et al. (2008) *J. Immunol.* 180: 559-68) independently of retinoic acid levels.

Figure 2:
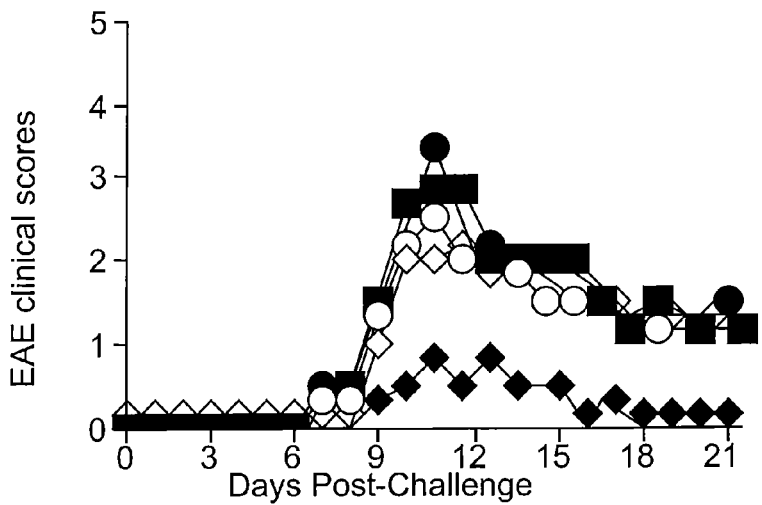
FIG. 2 shows that adoptive transfer of converted cells from CD4+ T cells of animals reconstituted with wild-type *B. fragilis* protected against subsequent EAE induction whereas converted cells from naïve, antibiotics-treated, or ΔPSA *B. fragilis* reconstituted mice did not confer any protection against the disease. *, P<0.01, represents statistical differences between groups.

These results show an enhanced capacity of conversion to FoxP3$^+$T$_{reg}$ cells by CD25$^-$T cells purified from MLN of mice reconstituted with wild-type *B. fragilis* when cells were cultured in the presence of IL-2, 0.5 or 5 ng/ml but no retinoic acid. Based on the significant differences in the conversion rate observed, the capacity of these converted FoxP3$^+$T$_{reg}$ cells to protect the development of EAE after adoptive transfer was determined. Cells cultured in 5 ng/ml of TGF-β and no retinoic acid were collected after 4 days and adoptively transferred. The results of this analysis showed that cells converted from CD4+ T cells of animals reconstituted with wild-type $B.$ $fragilis$ protected against subsequent EAE induction whereas converted cells from naïve, antibiotic-treated, or ΔPSA $B.$ $fragilis$ reconstituted mice did not confer any protection against the disease (FIG. 2).

Figure 4:
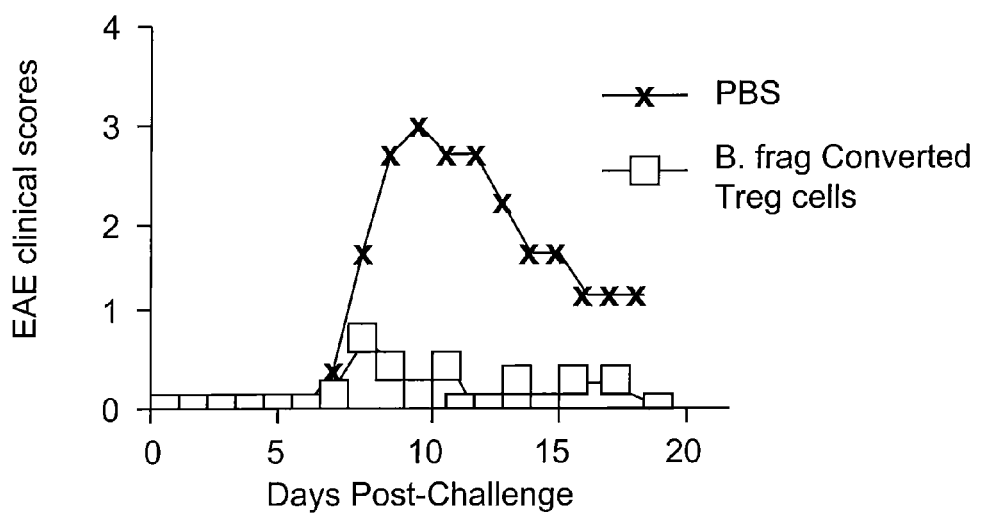
FIG. 4 shows therapeutic adoptive transfer of regulatory T cells provides protection against EAE. Naïve CD4+ T cells from mice treated with antibiotics and subsequently colonized with *B. fragilis* showed enhanced rates of conversion into $T_{reg}$ cells. FoxP3+ converted cells were sorted and adoptively transferred (1×10$^6$ cells/mouse) into naïve recipient mice four days after EAE was induced.

When $B.$ $fragilis$ converted $T_{reg}$ cells were adoptively transferred into naïve mice 4 days after EAE induction, a significant reduction in the EAE clinical scores average was observed. These results indicate a therapeutic effect of converted $T_{reg}$ cells of mice reconstituted with PSA-producing $B.$ $fragilis$ (FIG. 4).

EXAMPLE 6

Regulatory T Cells Induced by Wild-Type $B.$ $Fragilis$ are Critical for Protection Against EAE To elucidate the potential role of regulatory T cells induced in vivo by reconstitution with wild-type or ΔPSA $B.$ $fragilis$ in the protection observed against EAE, adoptive transfer experiments were conducted. In the first experiment, the protective role of CD4$^+$ or CD8$^+$ T cells was compared. SJL mice were treated for seven days with ampicillin, vancomycin, neomycin sulfate and metronidazole dissolved in drinking water, or with normal drinking water (naïve control group). After the treatment, CLN were harvested and CD4+ or CD8$^+$ T cell populations were enriched by selection with magnetic microbeads. Adoptive transfer of 1×10$^6$ cells/mouse 96% pure) was performed 1 day prior to EAE induction with PLP$_{139-151}$. CD4$^+$ T cells isolated from CLN of mice treated with antibiotics significantly reduced the EAE clinical scores of SJL mice when compared to CD4$^+$ T cells obtained from naïve mice. By contrast, no significant differences were observed in the clinical outcome of the disease after adoptive transfer of CD8$^+$ T cell-enriched population from CLN of mice treated with antibiotics when compared to PBS treated mice or mice treated with naïve CD8$^+$ T cells. These results indicate that CD8$^+$ T cell of mice treated with antibiotics do not play a role in the protection against EAE observed previously.

It was next determined whether CD25$^+$CD4$^+$ or CD25$^-$CD4$^+$ T cells obtained from CLN of mice treated with antibiotics would be suppressive in vitro and would confer protection against EAE after adoptive transfer. The suppressive capacity of antibiotics treated FoxP3-enriched CD25$^+$CD4$^+$ T cells was significantly enhanced at 1:10 $T_{supp}$:$T_{effector}$ ratio. Despite the statistical significance at one single cell ratio, it is possible that the observation might have no biological relevance. In order to analyze a potential protective role of these cell populations, naïve recipient SJL mice were adoptively transferred with 4×10$^5$ cells/mouse of CD25$^+$CD4$^+$ or CD25$^-$CD4$^+$ T cells obtained from CLN of naïve or mice previously treated with antibiotics one day prior EAE induction with PLP$_{139-151}$. When CD25$^+$CD4$^+$ T cells (>75% FoxP3$^+$) purified from CLN of SJL mice treated with antibiotics a significant reduction of the EAE clinical scores was observed. No protection was observed after adoptive transfer of the control arms including CD25$^-$CD4$^+$ T cells purified from mice treated with antibiotics, CD25$^+$CD4$^+$ and CD25$^-$CD4$^+$T cells obtained from naïve mice.

Analysis of the cytokine profile of adoptively transferred CD25+CD4$^+$ and CD25–CD4+ T cells showed that protective CD4$^+$CD25$^+$ T cells (>75% FoxP3$^+$) sorted from mice treated orally with antibiotics produced significantly enhanced levels of IL-10 (P<0.01) and IL-13 (not significant) when compared to naïve CD4$^+$CD25$^+$ T cells. When CD25$^-$CD4$^+$T cells were compared, those obtained from oral-treated mice showed significant reductions in IFN-γ and IL-17, and no significant differences in IL-10 and IL-13 when compared to naïve levels.

To confirm the protective capacity of the $T_{reg}$ cells from oral antibiotic treated mice, in vivo neutralization of CD25-expressing cells was performed using a depleting anti-CD25 mAb (clone PC-61). Two doses of 300 µg/mouse on days 3 and 5 after the initiation of oral antibiotic treatment reduced the CD25$^+$ in CD4$^+$ T cells of naïve mice as well as mice treated with either oral or i.p. with antibiotics when compared to control treatment with rat IgG isotype control. Partial reversion of protection was observed by depletion of CD25$^+$ T cells in mice treated with oral antibiotics. The onset of clinical disease occurred earlier (P<0.05) in all groups treated with anti-CD25 mAb when compared to rat IgG treated mice (Table 3). The cumulative scores and mortality of mice treated orally with antibiotics and subsequently with anti-CD25 mAb were significantly more severe (P<0.05) when compared to mice treated orally with antibiotics and injected with rat IgG (Table 3). EAE clinical scores were also significantly reduced in CD25-neutralized mice previously treated with antibiotics when compared to either naïve (P<0.05) or i.p. treated (P<0.05) mice.

Figure 3:
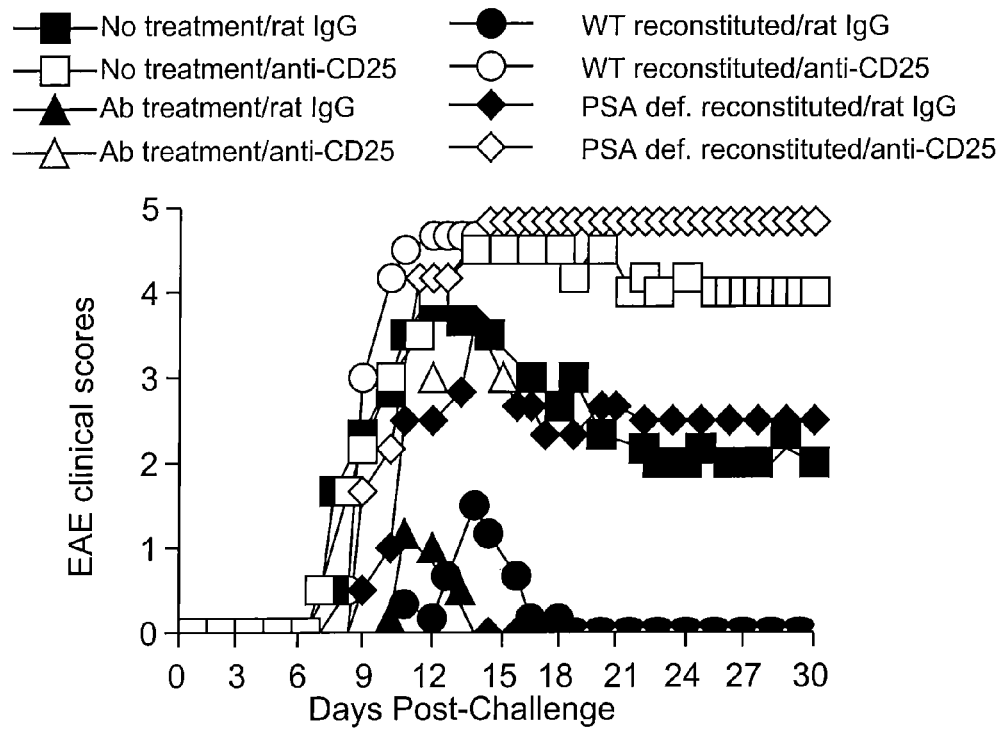
FIG. 3 shows that CD25+CD4+ T cells from wild-type *B. fragilis* reconstituted mice confer protection against EAE. CLN of mice treated with antibiotics and subsequently reconstituted with wild-type or ΔPSA *B. fragilis* were harvested and CD4+CD25− (FoxP3+≈10%) and CD4+CD25+ T cells (FoxP3+≥75%) were sorted by FACS and adoptively transferred (4×10$^5$ cells/mouse) into naïve recipient SJL mice. One day after adoptive transfer, mice were EAE induced with $PLP_{139-151}$. Treatment with anti-CD25 MAb reduced very significantly the CD25+ percentages in CD4$_+$ T cells of naïve, Ab-treated and reconstituted mice when compared to treatment with rat IgG isotype control. When EAE was induced, protection observed in mice treated with antibiotics and reconstituted with WT *B. fragilis* was lost. Depicted are the combined results from two separate experiments for a total of 8 mice/group: *, P<0.01 for naïve vs. oral treatment and oral vs. i.p. treated mice.

To further analyze adoptive transfer, CLN of mice treated with antibiotics and subsequently reconstituted with wild-type or ΔPSA $B.$ $fragilis$ were harvested seven days after bacterial reconstitution. CD4$^+$CD25$^-$ (FoxP3$^+$≈10%) and CD4$^+$CD25$^+$ T cells (FoxP3$^+$≥75%) adoptively transferred (4×10$^5$ cells/mouse) into naïve recipient SJL mice. One day after adoptive transfer, mice were EAE induced with PLP$_{139-151}$. The results showed that adoptive transfer of CD4$^+$CD25$^+$ T cells from CLN of mice treated with antibiotics, and from mice reconstituted with wild-type $B.$ $fragilis$ reduced significantly the EAE clinical scores when compared to PBS control mice (FIG. 3). When CD4$^+$CD25$^+$ T cells of ΔPSA $B.$ $fragilis$ reconstituted mice were transferred, a reduced level of protection was observed. No protection was conferred by adoptively transferred CD4$^+$CD25$^-$ T cells from CLN of mice treated with antibiotics, or from mice reconstituted with ΔPSA $B.$ $fragilis$. By contrast, a partial reduction of EAE clinical scores was observed when CD4$^+$CD25$^-$ T cells from wild-type $B.$ $fragilis$ reconstituted cells were transferred.

In vivo experiments of CD25 depletion were performed in order to confirm their critical role in the control of EAE development. Mice subjected to treatment with antibiotics and bacterial reconstitutions were treated i.p. with two doses of anti-CD25 mAb (PC61) before EAE induction. Antibody treatment reduced significantly the CD25$^+$ T cell populations in lymph nodes and whole blood samples in all groups.

These results indicate that the EAE protection observed in mice reconstituted with wild-type $B.$ $fragilis$ could be driven by different suppressive populations of CD4$^+$CD25$^-$ and CD25$^+$ T cells. This observation indicates that gut commensal bacteria play an important role in the regulation of CNS demyelination and this regulatory effect can be under the control of specific bacterial antigens such as the capsular polysaccharide A antigen of the human commensal $B.$ $fragilis$.

EXAMPLE 7

PSA-Producing $Bacteroides$ $Fragilis$ Impair EAE Development in SJL Mice

As described herein, alterations in the immune profile in germ-free mice demonstrates a default Th2 bias and a significant reduction in proinflammatory IL-17-producing CD4+ T cells compared to mice with an intact communal gut bacterial profile (Niess, et al. (2008) *J. Immunol.* 180:559). SJL were treated with antibiotics to deplete gut microbiota. To ascertain whether colonization with *B. fragilis* could influence the development of experimental autoimmune encephalomyelitis, the protective effect of wild-type and PSA-deficient *B. fragilis* against CNS autoimmune disorders was assessed. Antibiotic treated SJL mice were colonized with $10^{10}$ CFU/mouse of wild-type *B. fragilis* and ΔPSA *B. fragilis* and EAE was induced with autoreactive $PLP_{139-151}$ following standard procedures one week after bacterial reconstitution. Oral treatment with antibiotics reduced significantly the severity of EAE clinical symptoms after induction with $PLP_{139-151}$ (FIG. 1). Subsequent colonization with wild-type *B. fragilis* of mice with diminished microflora maintained the reduced EAE susceptibility. While clinical onset for normal SJL mice followed the expected EAE clinical outcome, mice treated with antibiotics and colonized with wild-type *B. fragilis* were resistant to the development of EAE, whereas the colonization of mice with ΔPSA *B. fragilis* rendered the mice susceptible to disease development. No protection was observed when naïve mice were colonized with *B. fragilis* or ΔPSA *B. fragilis*.

To demonstrate the role of PSA in protection against EAE, mice were treated orally with 50 μg of purified PSA every other three days after EAE induction. Results showed a significant reduction in the EAE clinical scores in mice treated with purified PSA.

It has been demonstrated that CD4+ T cell activation by PSA is dependent on the presentation of the antigen by CD11c+ dendritic cells (Duan, et al. (2008) *Proc. Natl. Acad. Sci. USA* 105:5183-8). After oral treatment of mice with fluorescence-labeled PSA, the polysaccharide is associated with CD11c+ dendritic cells (DCs), but not CD4+ T cells or CD19+ B cells, in the mesenteric lymph nodes (MLNs), suggesting that DCs sample PSA from the intestine and migrate to the MLNs to initiate an immune response. The role of $CD11c^{high}CD103^+$ DCs in the conversion of naïve CD4+ T cells into $Foxp3^+T_{reg}$ cells has been demonstrated (Coombes, et al. (2007) *J. Exp. Med.* 204:1757-64).

In the present analysis, it was determined whether MLN $CD11^{high}CD103^+$ DCs in the presence of anti-inflammatory environment could play a role inducing $T_{reg}$ cell differentiation in mice immunized with PSA of *B. fragilis*. FACS analysis showed that the treatment with PSA significantly enhanced the percentages of these $CD11c^{high}CD103^+$ DCs. These observations indicate that $CD11c^{high}CD103^+$ DCs are involved in the regulation exhibited by exposure to PSA antigen.

What is claimed is:

1. A method for treating an autoimmune disease comprising administering to a first subject an antibiotic; administering to the first subject exogenous *Bacteroides*; isolating a $CD25^+CD4^+$ T cell population comprising at least 75% $FoxP3^+$ $CD25^+CD4^+$ regulatory T cells from the first subject colonized with the exogenous *Bacteroides*; and administering said T cell population to a second subject having an autoimmune disease so that the autoimmune disease is treated.

2. The method of claim 1, wherein the *Bacteroides* is *Bacteroides ovatus, B. thetaiotaomicron, B. fragilis,* or *B. intestinalis*.

3. The method of claim 1, wherein the autoimmune disease is multiple sclerosis.

* * * * *